United States Patent [19]

Zotto et al.

[11] Patent Number: 4,988,504

[45] Date of Patent: Jan. 29, 1991

[54] SILICONE SURFACTANTS

[75] Inventors: Anthony A. Zotto, Troy; Raymond J. Thimineur, Scotia; William J. Raleigh, Rensselaer, all of N.Y.

[73] Assignee: General Electric Company, Waterford, N.Y.

[21] Appl. No.: 87,051

[22] Filed: Aug. 19, 1987

[51] Int. Cl.$^5$ .................................................. A61K 7/32
[52] U.S. Cl. ........................................ 424/65; 514/63; 556/445; 556/439
[58] Field of Search ...................... 424/68, 65, 66, 67; 514/63; 556/445, 423, 439

[56] References Cited

U.S. PATENT DOCUMENTS

| Re. 25,727 | 2/1965 | Haluska . | |
|---|---|---|---|
| 2,868,824 | 1/1959 | Haluska . | |
| 3,172,899 | 3/1965 | Bailey . | |
| 3,174,987 | 3/1965 | Simmler et al. . | |
| 3,234,252 | 2/1966 | Pater . | |
| 3,600,418 | 8/1971 | Bailey et al. . | |
| 4,122,029 | 10/1978 | Gee et al. | 252/309 |
| 4,218,250 | 8/1980 | Kasprzak | 106/3 |
| 4,265,878 | 5/1981 | Keil | 424/68 |
| 4,268,499 | 5/1981 | Keil | 424/68 |
| 4,311,695 | 1/1982 | Starch | 424/184 |
| 4,515,979 | 5/1985 | Oesuki et al. | 556/445 |
| 4,725,432 | 2/1988 | May | 424/68 |
| 4,784,844 | 11/1988 | Thimineur et al. | 424/65 |
| 4,801,447 | 1/1989 | Gum | 424/68 |
| 4,814,409 | 3/1989 | Blevins, II et al. | 556/445 |
| 4,822,603 | 4/1989 | Farris et al. | 424/66 |

FOREIGN PATENT DOCUMENTS 8503641 8/1985 PCT Int'l Appl. .................. 424/65

Primary Examiner—H. M. S. Sneed
Assistant Examiner—J. Saba

[57] ABSTRACT

Certain polysiloxane surface active agents containing radial organic polyether groups provide for improved stability of silicone emulsions, particularly antiperspirant stick compositions.

20 Claims, No Drawings

SILICONE SURFACTANTS

The present invention relates to surface active agents of polysiloxane. More particularly, the present invention relates to polysiloxane surface active agents having radial organic polyether groups for use in stabilizing silicone emulsions.

BACKGROUND OF THE INVENTION

The use of polysiloxane surface active agents containing radial organic polyether groups to stabilize silicone emulsions is well known. U.S. Pat. No. 4,265,878 uses a polysiloxane surface active agent to stabilize antiperspirant stick compositions. U.S. Pat. No. 4,218,250 uses such a polysiloxane surface active agent to stabilize polish formulations. U.S.

No. 4,268,499 uses these surface active agents to stabilize antiperspirant emulsion compositions. Further, U.S. Pat. No. 4,311,695 uses such surface active agents in personal care creams and the like.

The subject Polysiloxane surface active agents are generically known and are sometimes referred to as siloxane-oxyalkylene copolymers. However, their use to date as stabilizers for silicone emulsions has not been completely satisfactory because the variables effecting their function are not well understood.

It is the object of the present invention to produce novel polysiloxane surface active agents containing radial organic polyether groups.

It is another object of the present invention to produce such polysiloxane surface active agents for polishes, sun screen oils, antiperspirant lotions, body lotions, and particularly for improved antiperspirant stick compositions.

It is another object of the present invention to produce such polysiloxane surface active agents for antiperspirant stick compositions having improved stability, remelt stability, and low wax content.

SUMMARY OF THE INVENTION

Briefly, there is provided by the present invention a surface active agent of polysiloxane comprising (a) units of the formula:

$$R_2SiO_{2/2}$$

where R is hydrogen or a substituted or unsubstituted hydrocarbon radical of from 1 to about 12 carbon atoms and (b) units of the formula $$R_2SiO_{2/2}$$

where $R^1$ is a polyalkylene ether of the formula:

$$-R_a^3-(OR^2)-_nOR^4$$

where $R^2$ is a $-CH_2-CH_2-$ group, $R^3$ is a substituted or unsubstituted alkylene group of from 1 to 20 carbon atoms, $R^4$ is the same as R, n has a value of from about 5 to about 20, and "a" is 0 or 1, with the proviso that the polysiloxane absent $R^1$ has a molecular weight of from about 10,000 to about 40,000 and the weight ratio of $R^1$ to polysiloxane absent $R^1$ is from greater than 15/85 to less than 35/65. These surface active agents may be combined with water, cyclic polysiloxane fluid, organic waxes and active ingredient, to produce antiperspirant sticks of improved properties.

In addition to the (a) and (b) units described above, the polysiloxane surface active agent may also include (c) units of the formula $$RSiO_{3/2}$$

and will of course include end capping units which are preferably $R_3SiO_{1/2}$ but may have one or more of the R groups replaced with $R^1$, hydroxy or alkoxy. The use of the units of (c) is not preferred and where used, they should constitute from about 0.1 to about 1% by number of siloxane units.

Suitable R groups include hydrogen, methyl, ethyl, vinyl, phenyl, trifluoropropyl, etc. Preferably, at least about 80% by number of all R groups are methyl.

$R^2$ may be $-CH_2CH_2-$, $-CH_2CH(CH_3)-$, $-CH_2C(CH_3)_2-$, $-CH_2CH_2CH_2CH_2-$, etc. However, it is preferred and even necessary to form emulsions herein that at least 50% by number of $R^2$ be $-CH_2CH_2-$. Most preferably, all of the $R^2$ units are $-CH_2CH_2-$.

It is critical herein that the number of repeating units of $R^1$, i.e. the value of n be between about 5 and 20. Thus, in the case of ethylene oxide as the repeating unit, the molecular weight of $R^1$ should be less than about 900. The preferred value of n is from 10 to 15, which likewise for ethylene oxide provides a molecular weight for $R^1$ of no more than about 700.

$R^3$ is the group which bonds the polyoxyalkylene segment to the polysiloxane. Preferably, this group is derived from alpha-beta unsaturated carboxylic acids or alcohols. Thus, $R^3$ may be $-CH_2CH_2CH_2-$, $-CH_2CH_2-$, $-CH_2CH_2CH_2CH_2-$, $-(CH_2)_{10}(C=O)-$ etc. Preferably, $R^3$ is $-CH_2CH_2CH_2-$. Otherwise, "a" could be 0 and the segments joined by $-O-$ which is the product of a condensation reaction between a condensable substituent on the polysiloxane and a condensable end group on polyalkylene oxide.

$R^4$ is the terminal group of the polyalkylene ether. The type of $R^4$ is not critical and may be selected from hydrogen, methyl, ethyl, propyl, butyl, phenyl, alkenyl, acetyl, etc. Preferably, $R^4$ is hydrogen.

The polysiloxane absent $R^1$ should have a molecular weight between about 10,000 and 40,000 and preferably between 25,000 and 35,000. Further, the weight ratio of $R^1$ to polysiloxane absent $R^1$ should range from greater than 15/85 to less than 35/65 on a weight basis. Preferably, this ratio is between about 20/80 to 30/70. Given this ratio and a value for n above, it is possible to calculate the ratio of (b) siloxane units to all other siloxane units for any given surfactant. It is preferred herein that this ratio be greater than about 10/400 and preferably greater than about 15/400. The upper limit of this ratio is not as important and can be generally determined from ratios already given.

The polysiloxane surface active agent may be prepared by well known methods. The preferred method is to introduce an alpha-beta unsaturated alcohol or carboxylic acid into the polymerization of alkylene glycols to produce a terminally unsaturated polyalkylene oxide. These terminally unsaturated polyalkylene glycols are subsequently added to silicon bonded hydrogens on suitable polysiloxanes. The addition reaction proceeds best in the presence of an active metal catalyst such as platinum.

The manufacture of the polysiloxane surface active agents is well known and understood. Methods of preparation are taught in U.S. Pat. Nos. 4,265,878; Re 25,727; 3,174,987; 4,122,029; 3,172,899, and hereby incorporated by reference.

Antiperspirant stick compositions having improved properties may be formulated using the polysiloxane surface active agent. Such compositions contain (A) from about 100 to 200 parts by weight water having the desired amount of active ingredient dissolved therein as a discontinuous phase in about 100 parts by weight of a continuous oil matrix containing (B) about 50 to 75% by weight cyclic polysiloxane fluid, (C) about 25 to 50% by weight of an organic wax, and (D) about 0.25 to 5% by weight of polysiloxane surface active agent.

The active ingredient may be an aluminum salt for antiperspirant effect, a perfume, a dye, etc., so long as it is soluble or dispersible in water or oil. Preferably, there should be no more than about 1 part by weight active ingredient dissolved or dispersed in each 1 part by weight of water.

Cyclic polysiloxane fluid for use herein is a fluid of the formula

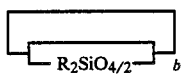

where b is 3, 4, 5, 6 or 7 and R is given above. It is important herein that the fluid evaporate from the skin at a rate which is slow enough not to make evaporative cooling noticeable but which is rapid enough that the skin quickly feels dry. Thus R and b should be chosen such that the boiling point of the cyclic polysiloxane fluid or blend of fluids is between about 175° and 250° C. Preferred polysiloxanes are octamethylcyclotetrapolysiloxane and decamethylcyclopentapolysiloxane.

Suitable organic waxes include mineral waxes, such as paraffin, etc; vegetable waxes, such as carnauba, flax, candelilla, etc.; and animal waxes such as bees wax. Chemically these waxes are branched or straight chain hydrocarbons, high molecular weight fatty acid, high molecular weight alcohols, or high molecular weight fatty acid esters. Characteristically waxes have low viscosities just above their melting point. For use herein the waxes should have a melting point between about 40° and 65° C. Such a melting point allows for proper application rates and prevents melting upon storage under ambient conditions. Preferably the organic wax is a mixture of waxes to control the hardness of the stick composition. Thus, a preferred organic wax is a mixture of a waxy ester for hardness, such as methyl hydroxystearate, and a solid alkanol such as stearyl alcohol. Where such a mixture of waxes is used, the organic wax might contain 10 to 50% by weight solid alkanol and 50 to 90% by weight waxy ester. Hardness is also greatly effected by the proportion of organic wax in the stick composition. Preferably, the continuous oil matrix contains about 25 to 40% by weight organic wax.

The antiperspirant stick is easily prepared by methods well known in the art. Herein the cyclic polysiloxane, organic wax, and polysiloxane surface active agent are heated until all components are liquid and then mixed. Generally the components will liquify between about 40 and 70° C. Subsequently the water solution with active ingredient is warmed and emulsified into the molten wax as is known. The warm emulsion is poured as close to solidification temperature as possible into molds and allowed to cool. The solid stick compositions containing the polysiloxane surface active agent described herein have improved stability and are drier than described in the prior art.

Other surfactants and additives may be included in the stick composition as experience has taught to be beneficial for specific formulations. For example, talc may be added to the oil phase and incorporated into the stick composition. Further, it may be known that further surfactants are beneficial to certain formulations, i.e. surfactants such as polyalkylene ethers, diglycerides, sorbitan monopalmitate, polyoxyethylene (20) sorbitan trioleate, complex fatty acid condensate, etc. The required or proper amount is well known to persons skilled in the art. The following examples are offered by way of illustration and not by way of limitation. All parts are in parts by weight.

SURFACTANTS 1 to 6

These examples illustrate the production of different polysiloxane surface active agents. Production requires as the principal inputs a polysiloxane hydride fluid and polyalkylene oxide having terminal unsaturation. Identification of the polysiloxane hydride fluid is based on the following nomenclature:

T = methyltrisiloxy unit
D = dimethyldisiloxy unit
M = trimethylsiloxy unit
$D^1$ = methylhydrogendisiloxy unit The polysiloxane hydride fluids shown herein are produced by acid equilibration of appropriate input materials. The molecular weight and structure for the base polysiloxane hydride fluid is shown for each surface active agent in Table I. The polyalkylene oxide having terminal unsaturation is an allyl alcohol initiate polymerization of ethylene oxide or a 50 by weight mixture of ethylene oxide with propylene oxide. The final molecular weight and monomer input for the polyalkylene oxide portion are indicated for each surface active agent in Table I. The functional polyalkylene oxide was diluted with toluene and azeotroped to eliminate water. Subsequently a platinum catalyst was added along with a stoichiometric amount of polysiloxane hydride fluid and the mixture was heated to 100° C. for 4 to 5 hours to insure complete reaction. The toluene was stripped and the resultant polysiloxane surface active agent was diluted to 10% by weight solution with cyclic $D_4$ and $D_5$ silicone fluid.

TABLE I

|  | 1 | 2 | 3 | 4 | 5 | 6 |
|---|---|---|---|---|---|---|
| Polysiloxane hydride fluid | 30,000 | 30,000 | 30,000 | 30,000 | 30,000 | 30,000 |
| Polysiloxane hydride fluid, structure | $MD_{400}D^1_{8.5}M$ | $MD_{380}D^1_{28}M$ | $MD_{400}D^1_{5.5}M$ | $MD_{400}D^1_{18}M$ | $TD_{400}D^1_{5.5}M_3$ | $TD_{400}D^1_{18}M_3$ |
| Polyalkylene oxide, MW | 1,800 | 550 | 1,800 | 550 | 1,800 | 550 |
| Ethylene Oxide/Propylene Oxide, # | 50/50 | 100/0 | 50/50 | 100/0 | 50/50 | 100/0 |
| Polysiloxane hydride | 65/35 | 65/35 | 75/25 | 75/25 | 75/25 | 75/25 |

TABLE I-continued

|  | 1 | 2 | 3 | 4 | 5 | 6 |
|---|---|---|---|---|---|---|
| fluid/Polyalkylene Oxide weight | | | | | | |

EXAMPLES 1 THROUGH 6

Antiperspirant sticks were manufactured using each of surface active agents in surfactants 1 through 6. Table II shows compositions for Part A and Part B. Part A contains as the surface active agent the corresponding surfactant 1 through 6. Part A is heated to 57° to 60° C. until all wax is melted and stirred to a homogeneous mixture. Likewise, Part B is heated to 57° to 60° C. Part B is added to Part A with continued mixing, and the resultant water in oil emulsion is cooled to just above melting. The emulsion is poured into commercially available stick containers which have been cooled in an ice box. Observations of each stick composition are noted in Table I.

TABLE II

|  | 1 | 2 | 3 | 4 | 5 | 6 |
|---|---|---|---|---|---|---|
| Part A | | | | | | |
| Surfactant | 1.0 | 1.0 | 1.0 | 1.0 | 1.0 | 1.0 |
| $D_4$ Fluid | 9.0 | 9.0 | 9.0 | 9.0 | 9.0 | 9.0 |
| $D_5$ Fluid | 15.0 | 15.0 | 15.0 | 15.0 | 15.0 | 15.0 |
| Stearyl Alcohol | 12.0 | 12.0 | 12.0 | 12.0 | 12.0 | 12.0 |
| Methyl Hydroxystearate | 3.0 | 3.0 | 3.0 | 3.0 | 3.0 | 3.0 |
| Sorbitan Mono-oleate | 0.1 | 0.1 | 0.1 | 0.1 | 0.1 | 0.1 |
| Part B | | | | | | |
| Aluminum Zirconium Chloride | 25.0 | 25.0 | 25.0 | 25.0 | 25.0 | 25.0 |
| Water | 34.9 | 34.9 | 34.9 | 34.9 | 34.9 | 34.9 |
| Observations | | | | | | |
| Stick Hardness | firm | soft | soft | firm | soft | soft |
| Stick Leakage | leak | leak | leak w/use | no leak | leak | leak |
| Stick Remelt | — | — | emulsion broken mixing does not restore | stable emulsion restored with mixing | — | — |

What is claimed is:

1. A polysiloxane surface active agent comprising:
   (a) units of the formula $R_2SiO_{2/2}$ where R is hydrogen or a substituted or unsubstituted hydrocarbon radical of from 1 to 12 carbon atoms;
   (b) units of the formula:

$RR^1SiO_{2/2}$ where $R^1$ is a polyalkylene ether of the formula:

$-R_a^3-(OR^2)_n-OR^4$ where $R^2$ is $-CH_2CH_2-$, $R^3$ is a substituted or unsubstituted alkylene group of 1 to 20 carbon atoms, $R^4$ is the same as R, n has a value of from 5 to about 20, and "a" is 0 or 1; and
   (c) endcapping units;
   with the proviso that the polysiloxane absent $R^1$ has a molecular weight of from about 25,000 to about 35,000 and the weight ratio of $R^1$ to polysiloxane absent $R^1$ is from greater than 15/85 to less than 35/65.

2. The polysiloxane surface active agent of claim 1 wherein about 80% by number of R is methyl.

3. The polysiloxane surface active agent of claim 1 wherein n has a value of from about 10 to about 15.

4. The polysiloxane surface active agent of claim 1 wherein $R^1$ has a maximum weight of less than about 900.

5. The polysiloxane surface active agent of claim 3 wherein $R^1$ has a molecular weight of about 700.

6. The polysiloxane surface active agent of claim 1 wherein $R^3$ is derived from a compound selected from the group consisting of alpha-beta unsaturated carboxylic acids and alpha-beta unsaturated alcohols.

7. The polysiloxane surface active agent of claim 1 wherein $R^3$ is selected from the group consisting of $-CH_2CH_2CH_2-$, $-CH_2CH_2-$, $-CH_2CH_2CH_2CH_2-$, and $-(CH_2)_{10}(C=O)-$.

8. The polysiloxane surface active agent of claim 1 wherein the weight ratio of $R^1$ to polysiloxane absent $R^1$ ranges from about 20/80 to about 30/70.

9. The polysiloxane surface active agent of claim 1 wherein the ratio of (b) units to all other siloxane units is greater than about 10/400.

10. The polysiloxane surface active agent of claim 1 wherein the ratio of (b) units to all other siloxane units is greater than about 15/400.

11. An antiperspirant stick composition comprising:
   (A) from about 100 to 200 parts by weight of water having an active ingredient dissolved therein; in a discontinuous phase in about 100 parts by weight of a continuous oil matrix containing:
   (B) about 50 to 75% by weight cyclic polysiloxane fluid;
   (C) about 25 to 50% by weight of an organic wax; and
   (D) about 0.25 to 5% by weight of a polysiloxane surface active agent comprising:
   (a) units of the formula:

$R^2SiO_{2/2}$ where R is hydrogen or a substituted or unsubstituted hydrocarbon radical of from 1 to 12 carbon atoms;
   (b) units of the formula:

$RR^1SiO_{2/2}$ where $R^1$ is a polyalkylene ether of the formula:

$-R_a^3-(OR^2)_n-OR^4$ where $R^2$ is a $-CH_2-CH_2-$ group, $R^3$ is a substituted or unsubstituted alkylene group of 1 to 20 carbon atoms, $R^4$ is the same as R, n has a value of from 5 to about 20, and "a" is 0 or 1; and
   (c) endcapping units;
   with the proviso that the polysiloxane absent $R^1$ has a molecular weight of from about 25,000 to about 35,000 and the weight ratio of $R^1$ to polysiloxane absent $R^1$ is from greater than 15/85 to less than 35/65.

12. The stick composition of claim 11 wherein said polysiloxane surface active agent has an $R^2$ of 100% by number $-CH_2CH_2-$.

13. The stick composition of claim 11 wherein said polysiloxane surface active agent has an n with a value of from 10 to about 15.

14. The stick composition of claim 11 wherein said polysiloxane surface active agent has a weight ratio of $R^1$ to polysiloxane absent $R^1$ of from about 20/80 to about 30/70.

15. The stick composition of claim 11 wherein said polysiloxane surface active agent has a ratio of (b) units to all other siloxane units greater than about 10/400.

16. The stick composition of claim 11 wherein said organic wax is a mixture comprising from 50 to 90% by weight solid alkanol.

17. The stick composition of claim 11 wherein said active ingredient is an aluminum salt for antiperspirant effect.

18. The stick composition of claim 11 wherein said cyclic polysiloxane fluid boils between about 175° and 250° C.

19. The stick composition of claim 11 wherein said organic wax has a melting point between about 40° and 65° C.

20. The stick composition of claim 11 wherein $R^3$ is derived from a compound selected from the group consisting of alpha-beta unsaturated carboxylic acids and alpha-beta unsaturated alcohols.

* * * * *

UNITED STATES PATENT AND TRADEMARK OFFICE
CERTIFICATE OF CORRECTION

PATENT NO.   :   4,988,504
DATED        :   January 29, 1991
INVENTOR(S)  :   Anthony A. Zotto, Raymond J. Thimineur, William J. Raleigh It is certified that error appears in the above-identified patent and that said Letters Patent is hereby corrected as shown below:

Column 3, line 54, after the word
"contain", please delete  "10 to 50%" and substitute therefor
--50 to 90%--.

Column 3, line 55, after the word "and"
please delete "50 to 90%" and substitute therefor --10 to 90%--.

Signed and Sealed this

Eighth Day of December, 1992

*Attest:*

DOUGLAS B. COMER

*Attesting Officer*    Acting Commissioner of Patents and Trademarks